(12) United States Patent
Lee

(10) Patent No.: US 9,295,684 B2
(45) Date of Patent: Mar. 29, 2016

(54) CREAM COMPOSITION ENHANCING SKIN ABSORPTION OF GLUCOSAMINE

(71) Applicant: Ming-Chen Lee, Taipei (TW)

(72) Inventor: Ming-Chen Lee, Taipei (TW)

( * ) Notice: Subject to any disclaimer, the term of this patent is extended or adjusted under 35 U.S.C. 154(b) by 397 days.

(21) Appl. No.: 13/912,679

(22) Filed: Jun. 7, 2013

(65) Prior Publication Data

US 2013/0330373 A1    Dec. 12, 2013

Related U.S. Application Data

(60) Provisional application No. 61/656,991, filed on Jun. 7, 2012.

(51) Int. Cl.

| | |
|---|---|
| A61K 36/00 | (2006.01) |
| A61K 31/7008 | (2006.01) |
| A61K 9/00 | (2006.01) |
| A61K 31/726 | (2006.01) |
| A61K 31/10 | (2006.01) |
| A61K 47/20 | (2006.01) |
| A61K 47/22 | (2006.01) |
| A61K 47/36 | (2006.01) |
| A61K 31/728 | (2006.01) |
| A61K 36/81 | (2006.01) |
| A61K 35/60 | (2006.01) |

(52) U.S. Cl.
CPC ........... *A61K 31/7008* (2013.01); *A61K 9/0014* (2013.01); *A61K 31/10* (2013.01); *A61K 31/726* (2013.01); *A61K 31/728* (2013.01); *A61K 36/81* (2013.01); *A61K 47/20* (2013.01); *A61K 47/22* (2013.01); *A61K 47/36* (2013.01); *A61K 35/60* (2013.01)

(58) Field of Classification Search
None
See application file for complete search history.

(56) References Cited

U.S. PATENT DOCUMENTS

| | | | | |
|---|---|---|---|---|
| 4,711,904 A | * | 12/1987 | Luzzi et al. | 514/464 |
| 6,579,543 B1 | * | 6/2003 | McClung | 424/728 |
| 6,645,482 B2 | * | 11/2003 | Theoharides | 424/78.05 |
| 2002/0037312 A1 | * | 3/2002 | Brown et al. | 424/449 |

FOREIGN PATENT DOCUMENTS

KR    2010131809 A   *   12/2010

* cited by examiner

*Primary Examiner* — Qiuwen Mi
(74) *Attorney, Agent, or Firm* — Muncy, Geissler Olds & Lowe, P.C.

(57) ABSTRACT

The present invention relates to a cream composition of glucosamine, including at least 10 wt %-15 wt % of glucosamine HCL, a methylsulfonylmethane component, a chondroitin component, and a cream base, wherein the composition promotes penetration of glucosamine from skin of affected area by synergistic interaction between components, in order to enhance absorption of human body.

10 Claims, 1 Drawing Sheet

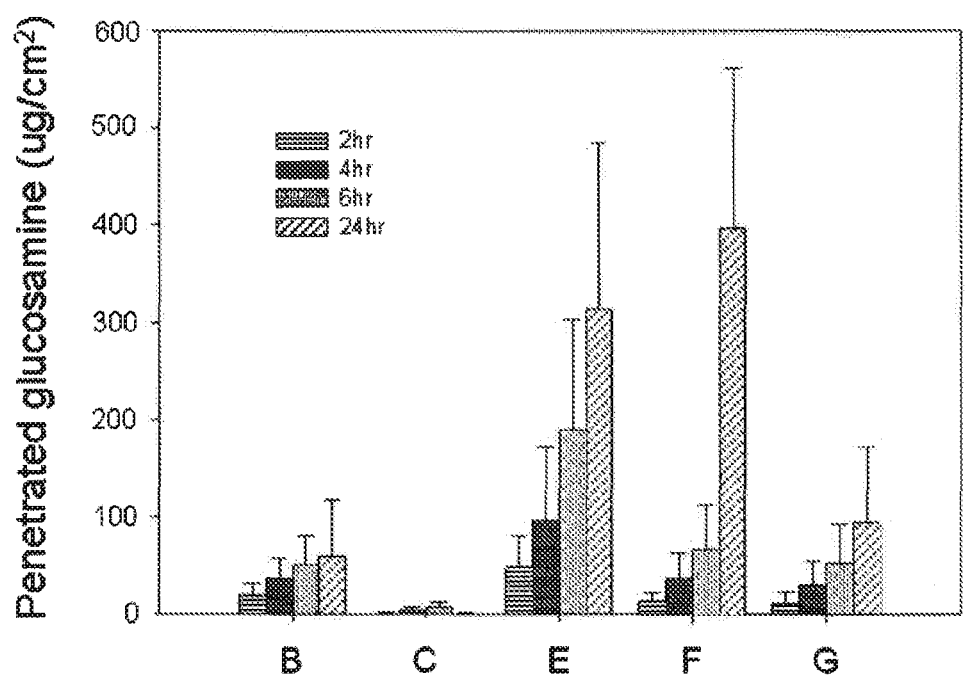

CREAM COMPOSITION ENHANCING SKIN ABSORPTION OF GLUCOSAMINE

CROSS REFERENCE TO RELATED APPLICATIONS

This application claims priority of U.S. Provisional Application No. 61/656,991 filed on Jun. 7, 2012 under 35 U.S.C. §119(e), the entire contents of all of which are hereby incorporated by reference.

BACKGROUND OF THE INVENTION

1. Field of the Invention

The present invention relates to a cream composition of glucosamine, and more particularly to a cream composition of glucosamine enhancing absorption of glucosamine through synergistic interaction of the composition.

2. Description of the Related Art

In recent years, the age of onset of degenerative arthritis has been continuously reduced. Degenerative arthritis tends to arise at patients' knee joints. Lately, researches prove that oral formulations of glucosamine are useful to promote joint cartilage growth and improve joint pain (disorder. However, only 1 of oral doses consumed works on the tissue of the affected region. Therefore, glucosamine formulations in the forms other than oral doses would be effective to focus the active ingredients on affected joints and worth investing effort in their development.

As a drug delivery system (DDS), ointment is proven effective in delivering active ingredients therein into skin. Thus it is believed that cream formulations can work similarly to form an active film on skin and facilitate active ingredients therein to be absorbed and used by skin. It is known that cream is made by dispersing aqueous phase and oil phases in the presence of an emulsifier. However, the high stickiness and thickness often make traditional cream disliked by users. In addition, when cream content in existing glucosamine HCL containing products is relatively high, the dispersing degree is lower, and even hydrolysis unfavorable for preservation may occur. As a result, existing glucosamine HCL containing products have cream content of only 5 wt %-10 wt %, without the effect of efficiently enhancing the absorption.

SUMMARY OF THE INVENTION

For improving the touch of cream, the inventor herein proposes a glucosamine cream composition with advanced formulation. To aqueous or oil components, emulsification can "reduce particle diameters and increase absorbability". By working with additional absorption enhancers and carriers, skin absorption thereto can be further improved, in order to enhance the absorption of glucosamine.

The present invention thus provides a cream composition enhancing skin absorption of glucosamine, which comprises:
 a) a glucosamine HCL of at least 10 wt % and at most 15 wt %;
 b) a methylsulfonylmethane component;
 c) a chondroitin component; and
 d) a cream base;
 contents of the composition cooperatively interact to promote the glucosamine infiltrate from skin of the affected region, thereby enhancing the absorption efficiency of human body.

The main objective of the present invention lies in: based on a principle of DDS, the larger the amount of active ingredients is, the more the active ingredients are absorbed by skin. The existing glucosamine-containing cream products typically have a glucosamine content of 5 wt %-10 wt %. For increasing the content of glucosamine HCL to 10 wt %-15 wt %, we need to overcome various challenges (saturation restricts the maximum level of glucosamine) through the manufacturing process, and we thus obtained the cream with 10 wt %-15 wt % of glucosamine HCL, based on the total weight of the cream composition, which represents the highest content currently available.

Another objective of the present invention is: the composition of the present invention is designed to be applied directly on skin over affected areas. After absorbed by the skin, the components, i.e. glucosamine HCL, methylsulfonylmethane and chondroitin, act synergistically and interactively to promote desired proliferation of cartilages and tissue fluid around the affected joints, thereby remedying degenerative arthritis. Further, a low-molecular-weight hyaluronic acid (HA) component, an Oligogeline component, an absorption enhancing component and a blood circulation promoting component are added, thereby enhancing the absorption of glucosamine through skin, and also suppressing inflammatory symptoms and easing pain.

Still another objective of the present invention is: existing cosmetics or cream composition usually use Polyethylene glycol (PEG) as a humectant, but PEG has been considered as a Carcinogen. Therefore, the present invention uses PEG free ingredients, thereby lowering use misgivings of health and safety.

BRIEF DESCRIPTION OF THE DRAWINGS

FIG. 1 is a statistic chart of experiment for derma penetration of glucosamine of the present invention.

DETAILED DESCRIPTION OF THE INVENTION

The present invention relates to a cream composition of glucosamine enhancing skin absorption of glucosamine, comprising:
 a) a cream base;
 b) at least 10 to 15 wt % glucosamine HCL, based on a total weight of the cream composition:

As a principle of DDS, the larger the amount of active ingredients is, the more the active ingredients are absorbed by skin. The existing glucosamine-containing cream products typically have a glucosamine content of lower than 10 wt %, because saturation restricts the maximum level of glucosamine. For increasing the content of glucosamine HCL to 10 wt %-15 wt %, we have overcome various challenges through the manufacturing process and obtain the cream with at least 10 wt %-15 wt % of glucosamine HCL, based on the total weight of the cream composition, which represents the highest content currently available,
 c) a methylsulfonylmethane component:

Methylsulfonylmethane (MSM) exists in many tissues, such as hair, skin, finger nails and so on. It has a molecular weight of 94, making it easy to be absorbed by skin.
 d) a chondroitin component:

According to researches, by taking shark cartilage, 70% of patients suffering arthritis (particularly osteoarthritis) and 60% of patients suffering chronic articular rheumatism reported pain relief, showing effectiveness better than medication. Shark cartilage is an effective cure for chronic articular rheumatism in virtue of the anti-angiogenesis proteins therein, which can eliminate blood capillaries around cartilages, and also in virtue of mucopolysaccharides therein, which can inhibit inflammatory symptoms. Shark cartilage is rich in natural minerals, including calcium and phosphorous, and thus can replenish bones and joints with nutrition.

The composition of the present invention is designed to be applied directly on skin over affected areas. After absorbed by the skin, the components, i.e. glucosamine HCL, methylsulfonylmethane and chondroitin, act synergistically and interactively to promote desired proliferation of cartilages and tissue fluid around the affected joints, thereby remedying degenerative arthritis.

Therein, the hyaluronic acid (HA) component is in an amount of 0.1 wt %-0.5 wt %; the methylsulfonylmethane component is in an amount of 1%-5 wt %, and the chondroitin component is in an amount of 1-5 wt %, both based on the total weight of the cream composition.

In addition, the cream base may include:

e) a low-molecular-weight hyaluronic acid (HA) component:

The low-molecular-weight hyaluronic acid (HA) has an average molecular weight of 5000-6000, with a particle size of about 25 nanometers, which can readily pass through the intervals between keratinocyte cells, so it can be easily absorbed by skin through sweat glands, cell intervals and pores. Low-molecular-weight hyaluronic acid, similar to high-molecular-weight hyaluronic acid, is effective in moisturizing skin and reducing wrinkles, and is further effective in suppressing inflammation and oxidation. The hyaluronic acid (HA) component is present in an amount of 0.1 wt %-1 wt %, based on the total weight of the cream composition.

f) an oligogeline component:

Oligogeline is a natural gel extract derived from chondrus crispus seaweed and is also known as "marine bandage" for its effectiveness in skin health restoration. When added in the cream base, it helps to evenly disperse and attach the components to the skin over affected joints, thereby improving the permeation of the active ingredients. It is present in an amount of 1 wt %-5 wt %, based on the total weight of the cream composition.

g) an absorption enhancing component:

The absorption enhancing component is herein dimethyl isosorbide (DMI), which is an organic solvent good for medication, facilitating uniform dispersion of active ingredients, which provides better absorbability. It is present in an amount of 1 wt %-36 wt %, based on the total weight of the cream composition.

h) a blood circulation promoting component:

The blood circulation promoting component is herein menthol or capsicum frutescens. Menthol and capsicum frutescens promote blood circulation, metabolism, and thereby skin absorption of active ingredients. Also, it adds fresh smell and cool touch to the skin where it is applied, so as to ease pain and uncomfortableness at the affected area. Menthol and capsicum frutescens are present in an amount of 0.1 wt %-1.0 wt %, based on the total weight of the cream composition.

With the formula disclosed above, the cream composition of the present invention is suitable for direct application to skin over affected joints, for the skin to absorb the components required by cartilage proliferation. After absorbed, these components can act directly on the affected tissues and improve the conditions of the targeted joints, thereby enhancing the absorbability of glucosamine.

For proving the invention actually has the effects above-mentioned, the inventor further proceeded following experiments of absorbability of glucosamine containing cream composition, and entrusted a credible third-party medical organization to process the experimental tests.

1) Organization: Mackay Memorial Hospital, Innovation & Incubation Center

2) Executor: Mackay Memorial Hospital, Department of Medical Research, Technical Officer, Chuang Chih Kuang 3) Experiment Design: Cortex Treatment of Nude Mouse The research uses cortex of back of nude mouse as research target. The cortex is cut off from the body of the animal, and the muscle on the cortex is removed by a surgical knife; afterward, neutral cleanser diluted with salt water is applied to cleanse oil and filth on the cortex. Next, the cortex is washed with normal saline for 3 to 5 times, and cut into pieces with perimeter of 2 cm×2 cm.

4) Transdermal Absorption Experiment:

All samples are tested repeatedly for six times, applying vertical Franz cell to test if the glucosamine is delivered transdermally by the formulation under the room temperature. The vertical Franz cell is separated into an upper chamber and a lower chamber, wherein the upper chamber is donor chamber and the lower one is receptor chamber. Before clipping in the subject cortex, the receptor chamber is filled with normal saline and settled with a miniature rotor. Next, the cortex is placed and clipped on the donor chamber with a metal clip. The formulation of 2 ml is added into the donor chamber, and the donor chamber is seal with parafilm. Next, the Franz cell is placed on an electromagnetic stirrer to spin the miniature rotor. Sample of 500 in the receptor chamber is taken out from the sampling port after 0, 2, 4, 6 and 24 hours, respectively, 5) Experimental Groups and Control Groups:

Table 1 is the formulation list of a first embodiment of the present invention, wherein group A is control group. Table 2 is the formulation list of a second embodiment of the present invention, wherein group D is control group.

TABLE 1

Formulation list of first embodiment

| Trade Name | INCI Name | A % | B % | C % |
|---|---|---|---|---|
| Glucosamine HCL | Glucosamine HCL | — | 10-15 | 10-15 |
| Emulgade 1000NI | Cetearly alcohol | 1-10 | 1-10 | 1-10 |
| DMI | Dimethyl isosorbide | 1-8 | 1-8 | 18-36 |
| Mineral oil | Mineral oil | 2-6 | 2-6 | 2-6 |
| Cyclic methicone 040 | Cyclic methicone | 6 | 6 | 6 |
| Dimethicone 350 | Dimethicone | 3 | 3 | 3 |
| Oligogeline | *Chondrus crispus* | 1-10 | 1-10 | 1-10 |
| Cetyl alcohol | Cetyl alcohol | 1-2 | 1-2 | 1-2 |
| Cyclic methicone 1000 | Cyclic methicone | 2 | 2 | 2 |
| Glycerol | Glycerol | 2 | 2 | 2 |
| Methylsulfonyl methane | Methylsulfonyl methane | 1-5 | 1-5 | 1-5 |
| Sodium chondroitin sulfate | Sodium chondroitin sulfate | 1-5 | 1-5 | 1-5 |
| Stearic acid | Stearic acid | 1-2 | 1-2 | 1-2 |
| Menthanol | Menthanol | 0.1-1 | 0.1-1 | 0.1-1 |
| Hyaluronate acid | Hyaluronate acid | 0.1-1 | 0.1-1 | 0.1-1 |
| Oleoresin capsicum | *Capsicum frutescens* | 0.1-1 | 0.1-1 | 0.1-1 |
| Grapefruit seed extract | *Citrus grandis* (grapefruit) Seed extract, glycerin | 0.3 | 0.3 | 0.3 |
| Cosmedia sp | Sodium polyacrylate | 0.1-1 | 0.1-1 | 0.1-1 |
| α-bisabolol | α-bisabolol | 0.5 | 0.5 | 0.5 |
| Allantoin | Allantoin | 0.3 | 0.3 | 0.3 |
| α-tocopherol acetate | α-tocopherol acetate | 0.1 | 0.1 | 0.1 |

TABLE 1-continued

Formulation list of first embodiment

| Trade Name | INCI Name | A % | B % | C % |
|---|---|---|---|---|
| H2O | Water | Added to 100% | Added to 100% | Added to 100% |

TABLE 2

Formulation list of second embodiment

| Trade Name | INCI Name | D % | E % | F % |
|---|---|---|---|---|
| Glucosamine HCL | Glucosamine HCL | — | 10-15 | 10-15 |
| DMI | Dimethyl isosorbide | 1-8 | 1-8 | 18-36 |
| Cyclic methicone 040 | Cyclic methicone | 6 | 6 | 6 |
| Mineral oil | Mineral oil | 3-6 | 3-6 | 3-6 |
| Dimethicone 350 | Dimethicone | 3 | 3 | 3 |
| Oligogeline | *Chondrus crispus* | 1-10 | 1-10 | 1-10 |
| Emulgade PL 68/50 | Ceteary glucoside (and)cetearyl alcohol | 1-5 | 1-5 | 1-5 |
| Cetyl alcohol | Cetyl alcohol | 1-3 | 1-3 | 1-3 |
| Cyclic methicone 1000 | Cyclic methicone | 2 | 2 | 2 |
| Glycerol | Glycerol | 2 | 2 | 2 |
| Methylsulfonyl methane | Methylsulfonyl methane | 1-5 | 1-5 | 1-5 |
| Sodium chondroitin sulfate | Sodium chondroitin sulfate | 1-5 | 1-5 | 1-5 |
| Stearic acid | Stearic acid | 1-3 | 1-3 | 1-3 |
| *Aloe* extract (10x) | *Aloe barbadensis* leaf extract | 1 | 1 | 1 |
| Menthanol | Menthanol | 0.1-1 | 0.1-1 | 0.1-1 |
| Xanthan gum | Xanthan gum | 0.1-1 | 0.1-1 | 0.1-1 |
| Ultragel 300 | Polyguaternium-37 | 0.1-1 | 0.1-1 | 0.1-1 |
| Hyaluronate acid | Hyaluronate acid | 0.1-1 | 0.1-1 | 0.1-1 |
| Oleoresin capsicum | *Capsicum frutescens* | 0.1-1 | 0.1-1 | 0.1-1 |
| Eumulgin SG | Sodium stearoyl glutamate | 0.1-1 | 0.1-1 | 0.1-1 |
| Grapefruit seed extract | *Citrus grandis* (grapefruit) seed extract, glycerin | 0.3 | 0.3 | 0.3 |
| α-bisabolol | α-bisabolol | 0.5 | 0.5 | 0.5 |

TABLE 2-continued

Formulation list of second embodiment

| Trade Name | INCI Name | D % | E % | F % |
|---|---|---|---|---|
| Allantoin | Allantoin | 0.3 | 0.3 | 0.3 |
| α-tocopherol acetate | α-tocopherol acetate | 0.1 | 0.1 | 0.1 |
| H2O | Water | Added to 100% | Added to 100% | Added to 100% |

6) Sample Analysis:

The sample of 50 ul taken out from the receptor chamber of the Franz cell is centrifugated with 12000 rpm for 30 minutes, whereby supernatant liquid is put into the analyzer tube of Liquid Chromatograph Tandem Mass Spectrometer. The Liquid Chromatograph Tandem Mass Spectrometer is operated under following circumstances: Separation column is the format of Luna silica 100A (2×50 mm. 5um). Mobile phase A is 0.01% formic acid, while Mobile phase B is 1 mM NH4OAc+ 0.1% formic acid in 100% acetonitrile. Elution of gradient is presented as Table 3. Main signal appears at about 2 to 3 minutes after elution begins. Measure of area under the signal is calculated with integral and compared with standard curve line to get a value D (ng/ml). By a formula, D (ng/ml)×volume of receptor chamber V (ml)÷total measure of area of transdermal cortex F ($cm^2$), penetration ratio P ($ng/cm^2$) is calculated.

TABLE 3

Operational Circumstances of Liquid Chromatograph Tandem Mass Spectrometer
Column: Luna silica 100 A (2 × 50 mm, 5 um)
Mobile phase A: 0.01% Formic acid
Mobile phase B: 1 mM NH4OAc + 0.1% FA in 100% Acetonitrile

| Step | Total Time (min) | Flow Rate (μl/min) | A (%) | B (%) |
|---|---|---|---|---|
| 0 | 0.00 | 600 | 10.0 | 90.0 |
| 1 | 0.10 | 600 | 10.0 | 90.0 |
| 2 | 0.50 | 600 | 50.0 | 50.0 |
| 3 | 2.00 | 600 | 50.0 | 50.0 |
| 4 | 2.30 | 600 | 10.0 | 90.0 |
| 5 | 5.00 | 600 | 10.0 | 90.0 |

7) Result:

Based on the analysis, colloid A and D do not contain glucosamine, and G is existing similar commodity on the market (Table 4). Based on the trend of 6-hour-penetration (FIG. 1), the best transdermal effect occur with E with 180 ug/$cm^2$, while effects of B, F and G are similar with 50 to 60 ul/$cm^2$, and effect of C is the lowest. In the value of 24-hour-penetration (Table 1), results of E and F are above 300 ug/$cm^2$, while effect of G is close to 100 ug/$cm^2$, and effect of B is close to 60 ug/$cm^2$.

TABLE 4

The statistics of transdermal absorption of 7 formulations from A to G, wherein glucosamine is not contained in A and D, thus A and D are not listed. (AVE: average value(ng/cm$^2$); SE: standard errors)

|  | 1 | 2 | 3 | 4 | 5 | 6 | AVE | SE |
|---|---|---|---|---|---|---|---|---|
| B-2 h | 50045 | 8369 | 0 | 60510 | 478 | 478 | 19980 | 11315 |
| B-4 h | 123214 | 24664 | 0 | 74490 | 323 | 642 | 37222 | 20838 |
| B-6 h | 163189 | 30596 | 0 | 112172 | 326 | 330 | 51102 | 28566 |
| B-24 h | 349596 | 1394 | 0 | 3089 | 967 | 651 | 59283 | 58064 |
| C-2 h | 0 | 1846 | 0 | 796 | 796 | 478 | 653 | 280 |
| C-4 h | 0 | 18844 | 0 | 1594 | 486 | 801 | 3621 | 3054 |
| C-6 h | 0 | 34854 | 0 | 2088 | 331 | 331 | 6257 | 5726 |
| C-24 h | 0 | 1223 | 0 | 1312 | 653 | 653 | 640 | 232 |
| E-2 h | 205732 | 0 | 57325 | 24994 | 287 | 430 | 48128 | 32832 |
| E-4 h | 471631 | 0 | 54471 | 49176 | 576 | 578 | 96072 | 75816 |
| E-6 h | 733210 | 91033 | 237433 | 65598 | 439 | 298 | 188019 | 114672 |
| E-24 h | 339962 | 1071865 | 461118 | 2114 | 444 | 444 | 312661 | 172299 |
| F-2 h | 60764 | 0 | 0 | 16338 | 287 | 287 | 12946 | 9923 |
| F-4 h | 163530 | 0 | 0 | 51774 | 853 | 433 | 36108 | 26843 |
| F-6 h | 280688 | 37261 | 0 | 83303 | 586 | 295 | 67022 | 44782 |
| F-24 h | 375096 | 232274 | 1186624 | 232118 | 25471 | 276317 | 396317 | 165018 |
| G-2 h | 0 | 0 | 0 | 64777 | 430 | 430 | 10939 | 10768 |
| G-4 h | 30669 | 0 | 0 | 145752 | 435 | 435 | 29548 | 23767 |
| G-6 h | 64885 | 0 | 0 | 247108 | 726 | 725 | 52241 | 40373 |
| G-24 h | 2108 | 82548 | 0 | 476834 | 591 | 447 | 93755 | 77771 |

According to the results above, the cream composition of the present invention actually enhance the absorption of glucosamine after 2, 4, 6 and even 24 hours, thereby achieving the objective efficiently.

What is claimed is:

1. A cream composition enhancing skin absorption of glucosamine, the cream composition comprising:
    at least 10 wt %-15 wt % of glucosamine HCL, based on a total weight of the cream composition;
    a methylsulfonylmethane component;
    a chondroitin component; and
    a cream base,
    wherein the components forming the composition act synergistically to facilitate the glucosamine component to permeate into skin of affected body areas, thereby enhancing human absorption of glucosamine.

2. The cream composition of claim 1, wherein the methylsulfonylmethane component is present in an amount of between 1 wt % and 5 wt %, and the chondroitin component is present in an amount of between 1 wt % and 5 wt %, both based on the total weight of the cream composition.

3. The cream composition of claim 1, wherein the cream base further comprises a low-molecular-weight hyaluronic acid (HA) component.

4. The cream composition of claim 1, wherein the low-molecular-weight hyaluronic acid (HA) component has a molecular weight of 5000-6000, and is present in an amount of between 0.1 wt % and 1 wt %, based on the total weight of the cream composition.

5. The cream composition of claim 1, wherein the chondroitin component is made from shark cartilage.

6. The cream composition of claim 1, wherein the cream base further comprises an Oligogeline component that is present in an amount of between 1 wt % and 10 wt %, based on the total weight of the cream composition.

7. The cream composition of claim 1, wherein the cream base further comprises an absorption enhancing component that is present in an amount of between 1 wt % and 36 wt %, based on the total weight of the cream composition.

8. The cream composition of claim 7, wherein the absorption enhancing component is dimethyl isosorbide (DMI).

9. The cream composition of claim 1, wherein the cream base further comprises a blood circulation promoting component that is present in an amount of between 0.1 wt % and 1 wt %, based on the total weight of the cream composition.

10. The cream composition of claim 9, wherein the blood circulation promoting component is menthol or *capsicum frutescens*.

\* \* \* \* \*